United States Patent [19]

Takeuchi et al.

[11] Patent Number: 5,033,468
[45] Date of Patent: Jul. 23, 1991

[54] BIO STIMULATING DEVICE

[75] Inventors: Mitunori Takeuchi, Sagamihara; Minoru Sasaki; Kazutaka Inoue, both of Yokohama, all of Japan

[73] Assignee: Kabusiki Kaisya Advance, Japan

[21] Appl. No.: 456,963

[22] Filed: Dec. 26, 1989

[51] Int. Cl.$^5$ ............................................. A61N 1/08
[52] U.S. Cl. ................................. 128/421; 128/420 R
[58] Field of Search .................. 128/421, 422, 423 R, 128/423 W, 420 R

[56] References Cited

U.S. PATENT DOCUMENTS

| 4,528,984 | 7/1985 | Morawetz et al. | 128/421 |
| 4,622,973 | 11/1986 | Agarwala | 128/421 |
| 4,653,479 | 3/1987 | Maurer | 128/423 W |
| 4,895,154 | 1/1990 | Bartelt et al. | 128/421 |

Primary Examiner—William E. Kamm
Assistant Examiner—Scott M. Getzow
Attorney, Agent, or Firm—Finnegan, Henderson, Farabow, Garrett & Dunner

[57] ABSTRACT

A bio-stimulating device including a signal controller unit for outputting at least a high frequency digital signal and a low frequency digital signal, a coil unit for changing the voltage of the digital signals input thereto from the control unit and having a first voltage changing function for high frequency digital signals and a second voltage changing function for low frequency digital signals, and an electrode unit including at least one electrode to be attached to a body wherein different kinds of electric pulses having different frequencies from each other can be generated, the size minimized, and energy saved.

20 Claims, 11 Drawing Sheets

BIO STIMULATING DEVICE

BACKGROUND OF THE INVENTION

1. Field of the Invention

This invention relates to a bio stimulating device having a digital signal control means and a voltage increasing means therein.

2. Description of the Related Art

There have recently appeared therapeutic devices which impart a certain level of voltage to the human body etc. in one of several stimulating modes, e.g., "pseudo-massage", "kneading", "thumping" or "pressing" mode selected by a microcomputer.

As different from this electrostimulating method, there has appeared an electrostimulating device using two high frequency oscillators to produse two outputs which produce stimulating pulses having a low frequency and large amplitude at portions inside the body where the high frequency electric energies cross.

These conventional electrostimulating devices utilize transformers or other coils to increase the source voltage input tens of times.

In these conventional devices, however, the voltage source and high frequency oscillators have never been assembled as an integral unit due to the significant difference in frequencies and output mechanisms.

Accordingly, a problem arises in that such conventional devices are large in size and difficult to carry.

Further, the energy consumed is large.

SUMMARY OF THE INVENTION

The object of the present invention is to provide a biostimulating device having a compact size and streamlined circuit which can reduce the electric energy used.

According to the present invention, there is provided a bio-stimulating device which includes a signal control means for outputting at least a high frequency digital signal and a low frequency digital signal, a coil means for changing the voltage of the digital signals input thereto from the control means and having a first voltage changing function for high frequency digital signals and a second voltage changing function for low frequency digital signals, and at least one electrode to be attached to a body for applying stimulating pulsed voltage.

DESCRIPTION OF THE PREFERRED EMBODIMENTS

The first embodiment of the present invention will be explained with reference to FIGS. 1 to 3.

According to the first embodiment, the bio-stimulating device basically includes a signal control means 50, a coil means 51, and an electrode means 52.

The signal control means 50 is provided with a digital signal control circuit 1 and amplifying circuits 2 and 3.

In the digital signal control circuit 1, there may be provided a digital signal generating circuit, a digital-/analog converter and analog/digital converter, if necessary, a high frequency digital signal generating oscillator, and a low frequency digital signal generating oscillator.

The digital signal control circuit 1 has at least two output terminals 11 and 12, the terminal 11 for the low frequency digital signal and the terminal 12 for the high frequency digital signal.

In the present invention, the signal output from the digital signal control circuit 1 may be either a digital signal or an analog signal.

Further, in the digital signal control circuit 1, a microcomputer may be provided to control the generation of a digital signal having a low and high frequency, control the duty ratio of the digital signals, control a switching circuit, later explained, or control a phase difference between two or more signals generated therefrom.

The driving digital pulse signal having low frequency dp1, output from the terminal 11, and the driving digital pulse signal having a high frequency dp2, output from the terminal 12 are connected to current or voltage amplifying circuits 2 and 3, respectively.

In the amplifying circuit, a source voltage V is amplified to a certain level by a transistor or the like provided therein.

The signals output from the amplifying circuits 2 and 3 are connected to anodes of diodes 4 and 5, respectively.

Each of the amplifying circuits 2 and 3 functions to turn ON-OFF the source voltage V by the driving pulse signal output from the digital signal control circuit 1 through a suitable switching means to the amplifying circuits.

The switching means may be provided between the digital signal control circuit 1 and the amplifying circuits 2 and 3 or provided in the digital signal control means 1.

Accordingly, a digital signal obtained by amplifying in the amplifying circuit, the source voltage with a transistor or the like in accordance with input digital driving pulses from the digital signal control circuit 1 can be output from the signal control means 50.

The coil means 51 functions to change the voltage of the digital signals output from the signal control means 50 and input thereto, for example, to increase the input voltage to a certain level.

It has a first voltage changing function for high frequency digital signals and a second voltage changing function for low frequency digital signals.

The coil means 51 is characterized in that it includes a coil 6 which can carry out the two functions by itself.

In one embodiment of the present invention, the coil means 51 is provided with a coil 6.

One end 27 is connected to a cathode of the diode 4 while the other end 29 is grounded.

Further, the coil 6 has a tapping portion 28 which is connected to a cathode of the diode 5.

While, in this embodiment, the coil means 51 is provided with a single coil 6, it may also consist of two or more electromagnetically coupled coils having different winding numbers.

The electrode means 52 is connected to the coil means 51 and is provided with at least two electrodes 31, 32, each of which is connected to one of the ends of the coil means.

In this embodiment, a load 7, which may be the human body, can be connected between the electrodes 31 and 32 when the device is used.

According to the present invention, the digital signal control circuit 1 may output a driving pulse signal with a desired pulse width or pulse interval varied in accordance with a program read from a memory device such as a ROM or RAM in a microcomputer or the like.

In the present invention, another digital signal processing means, for example, a custom IC or semi-custom IC, can be used in the digital signal control circuit 1, instead of a microcomputer.

Figure 1:
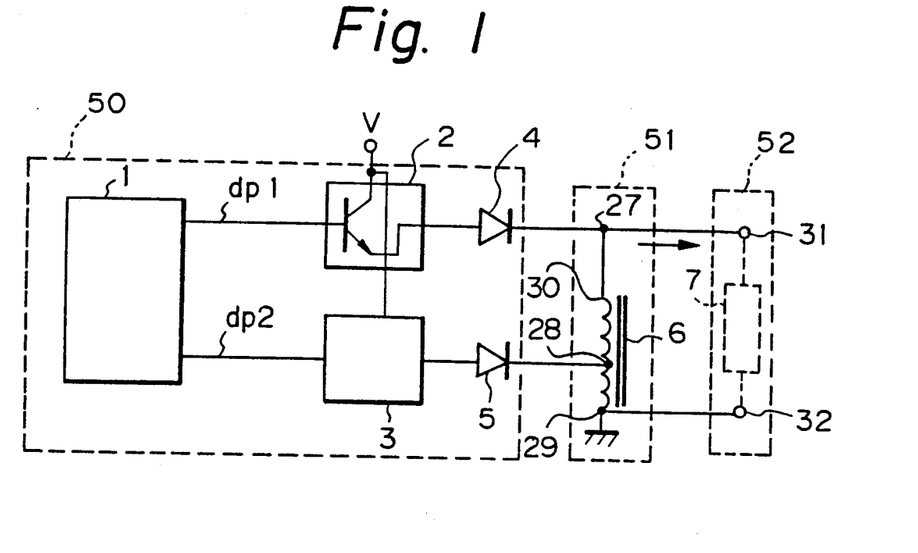
FIG. 1 is a diagram of a basic circuit of a first embodiment of the present invention.
Figure 2A:
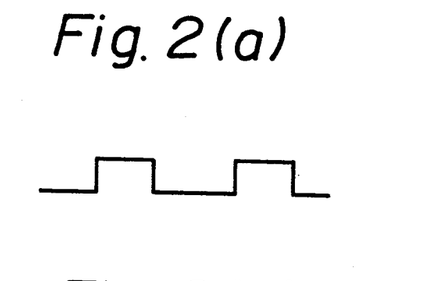
FIGS. 2(a) and 2(b) and 3(a) and 3(b) show waveforms of input digital signals and an output voltage of a coil means used in the embodiment shown in FIG. 1.
Figure 2B:
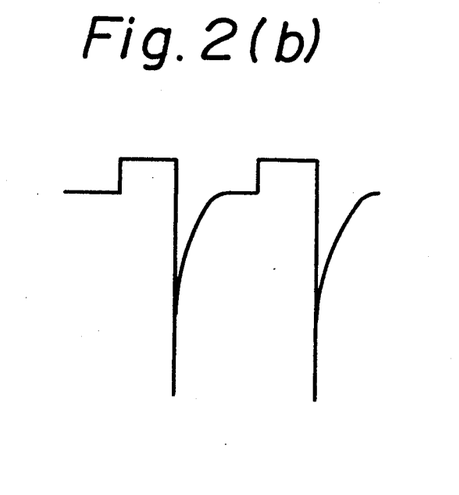
Figure 3A:
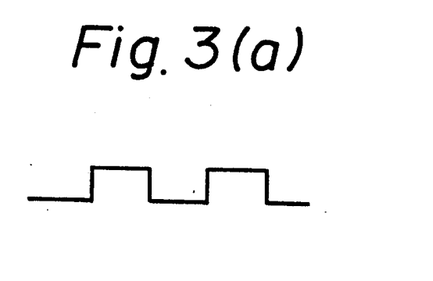
Figure 3B:
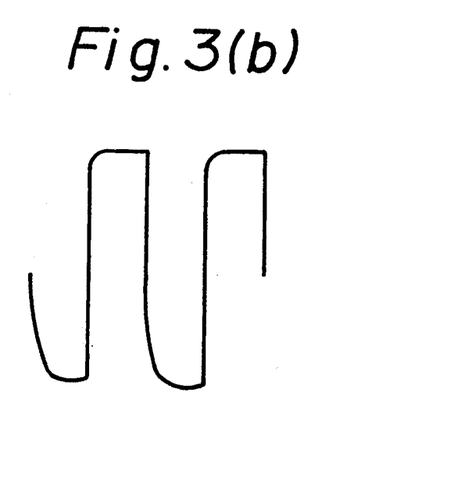

FIGS. 2 and 3 show waveforms taken at the points 27 and 28 in the circuit shown in FIG. 1, respectively.

As mentioned above, the coil means 51 has two functions for changing the voltage.

The second voltage changing function will be explained with reference to FIGS. 1 and 2.

When a low frequency driving pulse signal dp1 having the waveform shown in FIG. 2 (a) is applied to the amplifying circuit 2, an amplified digital signal is output from an output terminal 25 of the amplifying circuit 2 and applied to one end 27 of the coil 6 through a diode 4.

The electromagnetic current flowing to the coil 6 is turned ON and OFF by the amplified driving pulse signal whereby a counter electromotive force several tens of times of the source voltage V is generated at the point 27, the waveform of which is shown in FIG. 2(b).

This high voltage pulse signal is applied to the human body through the electrodes 31 and 32 to stimulate the portion to be treated.

The first voltage changing function will be explained with reference to FIGS. 1 and 3.

When a a high frequency driving pulse signal dp2 having the waveform shown in FIG. 3 (a) is applied to the amplifying circuit 3, an amplified digital signal is output from an output terminal 26 of the amplifying circuit 3 and applied to a tapped portion 28 of the coil 6 through a diode 5.

The voltage of the driving pulse signal is increased in accordance with a winding ratio $N_1/N_2$ between the number of coils $N_1$ of the coil 6 between the points 29 and 30 and $N_2$ between the points 28 and 29.

The increased high voltage signal with the waveform shown in FIG. 3 (b) is output between the ends 27 and 29 of the coil 6.

Figures 5A, 5B, 5C:
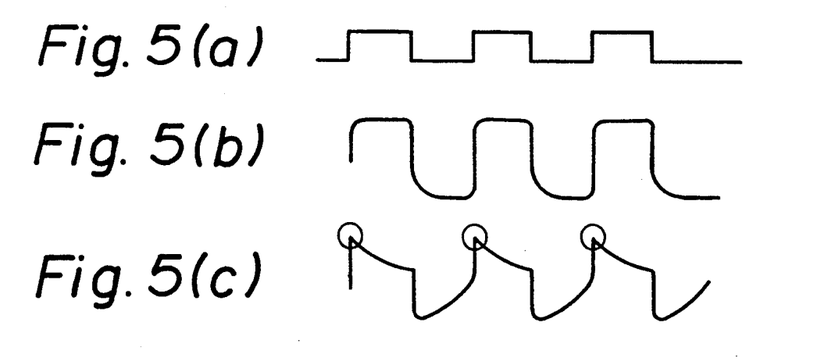
FIGS. 5(a) through 5(c) and 6(a) through 6(c) show waveforms of input digital signals, an output voltage of a coil means, and a current output from the coil means used in the embodiment shown in FIG. 4.

Since, in this embodiment, the digital pulse signal is controlled utilizing a computer or the digital circuit as mentioned above, the signal output from the digital signal control circuit 1 has a rectangular waveform as shown in FIG. 5 (a).

When the coil of the coil means 51 is driven by the signal, a peak electric current is generally generated at the output of the coil means 51 caused by the high frequency wave component in the current waveform in FIG. 5 (c) (the peaks are shown by circles).

This leads to deterioration of the efficiency of the electric current.

FIG. 5 (b) shows the amplified voltage waveform output from the coil 6.

The peak component of the output current causes significant electric power losses as well as is an obstacle in reducing the size of the whole circuit because it requires a maximum allowance for the circuit.

Thus, a means for eliminating such a peak current from the single output signal from the coil means is necessary.

Figure 4:
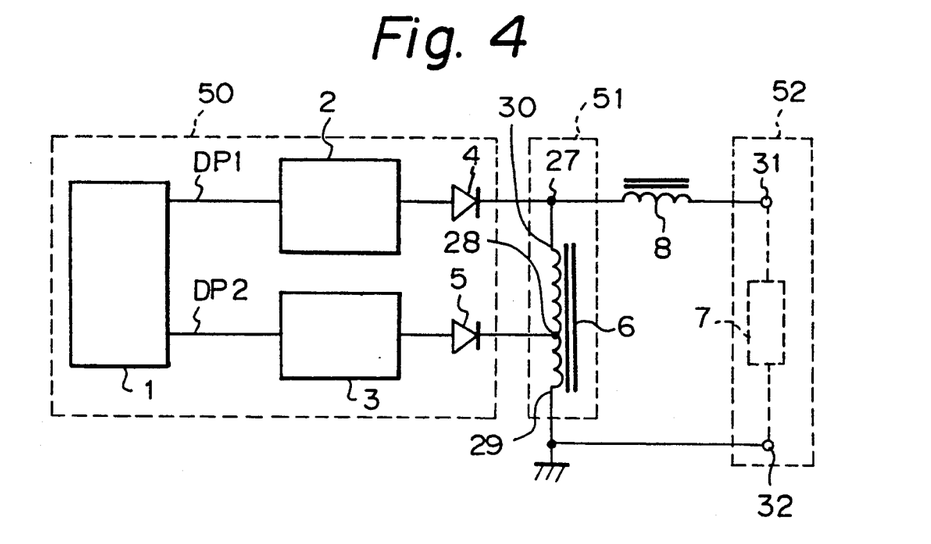
FIG. 4 is a diagram of a circuit of a second embodiment of the present invention.

The second embodiment of the present invention provides a bio-stimulating device having a circuit means eliminating such a peak current from the output signal.

This will be explained with reference to FIG. 4.

As shown in FIG. 4, almost all the components are as the same as used in FIG. 1 except for a coil 8 provided between the end 27 of the coil 6 and the electrode 31.

The low frequency driving pulse signal is not output while the high frequency driving pulse signal is output.

Figures 6A, 6B, 6C:
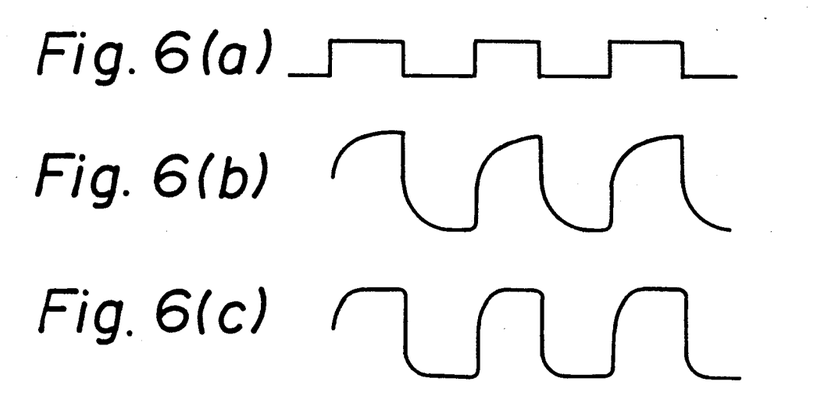

The high frequency pulse signal with the waveform as shown in FIG. 6 (a) is applied to the tap portion 28 of the coil 6.

The waveform of the signal output at the point 27 is shown in FIG. 6(b).

The waveform of the current output at the point 27 is shown in FIG. 6(c).

From the waveform, it is apparent that the peak component of the output current at the output of the coil 27 is completely eliminated.

Another embodiment for eliminating a peak current from the output current waveform generated by a high frequency digital pulse signal will be explained hereunder with reference to FIG. 7 as a third embodiment.

Figure 7:
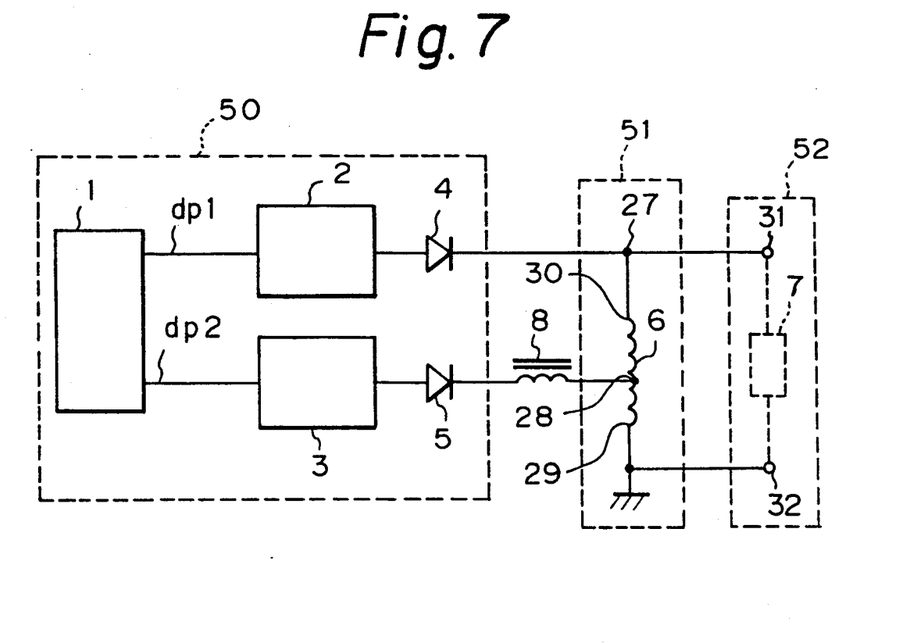
FIG. 7 is a diagram of a circuit of a third embodiment of the present invention.

As shown in FIG. 7 almost all the components are the same as used in FIG. 1 except for a coil 8 provided between the cathode of the diode 5 and the tap portion 28 of the coil 6.

The high frequency pulse signal with the waveform as shown in FIG. 6 (a) is applied to the tap portion 28 of the coil 6.

The waveform signal output at the point 27 is shown in FIG. 6(b).

Note that, in this embodiment, a low frequency driving pulse signal is not output while the high frequency driving pulse signal is output.

In FIG. 8 (a) is the waveform of the high frequency pulse signal input to the tap portion 28 through the amplifying circuit 3, the diode 5, and the coil 8, (b) is the waveform of the voltage obtained at the output of a primary coil portion defined between the point b and c of the coil in FIG. 7, while (c) is the waveform of the voltage obtained at the output of a secondary coil portion defined between the point a and c, and (d) is the waveform of the output current generated across the electrodes 31 and 32 via a load 7.

Figure 8A:
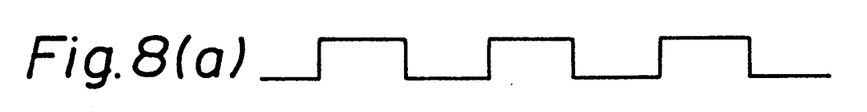
FIGS. 8(a) through 8(d) shows waveforms of input digital signal, an output voltage of a coil means, and a current output from the coil means used in the embodiment shown in FIG. 7.
Figure 8B:
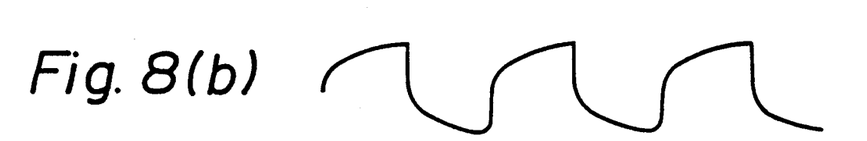
Figure 8C:
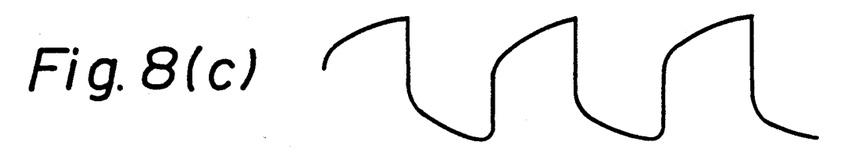
Figure 8D:
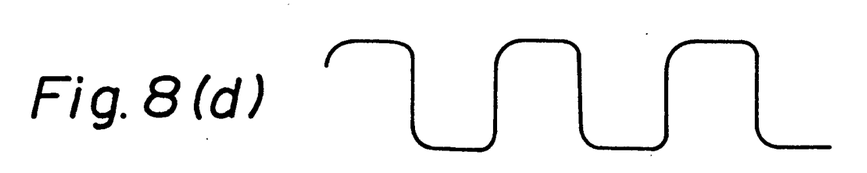

As apparent from the waveform (d), there is no peak component of the output current observed, so, the adverse effect on the current efficiency caused by the high frequency component can be eliminated by previously passing the high frequency pulse signal to the coil 6 through the coil 8.

Namely, it is preferable to provide a means, mainly comprising a coil, for eliminating a peak current caused by a high frequency component from the waveform output from the coil means 51, between the output terminal of the coil means 51 and the electrodes means or between the terminal of the signal control means 50 and the input terminal for the high frequency digital signals of the coil means 51.

On the other hand, when a low frequency pulse signal is used, the user sometimes feels uncomfortable due to the direct current component applied to the body.

Figures 10A, 10B, 10C:
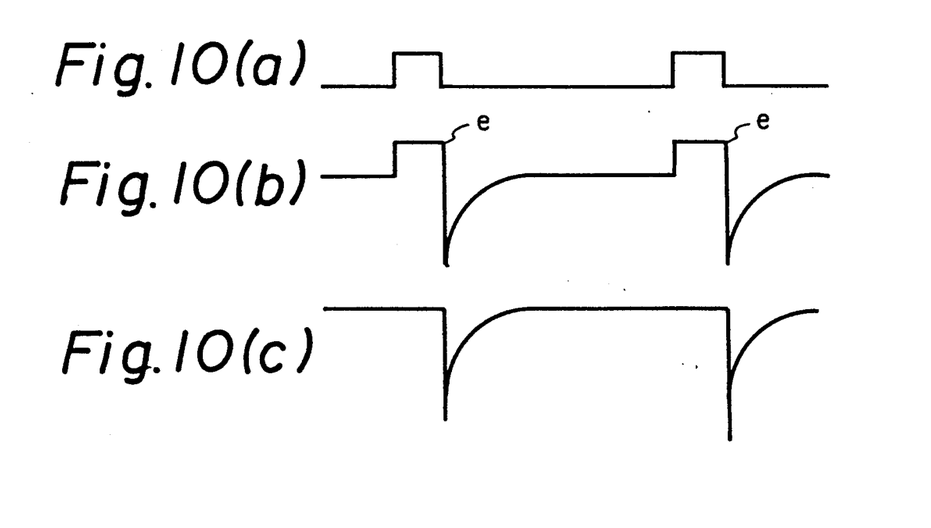
FIGS. 10(a) through 10(c) shows waveforms of input digital signals, an output voltage of a coil means, and current output from the coil means used in the embodiment shown in FIG. 9.

As shown in FIG. 10, when a low frequency pulse signal (a) is applied to the coil means 51 of the circuit shown in FIG. 1, the wave form of the output pulse generated across coil means 51 becomes as indicated by waveform (b), which is the same shown in FIG. 2(b).

The waveform (b) has a direct current component (e) which is uncomfortable to the human body as explained above and should be eliminated.

Figure 9:
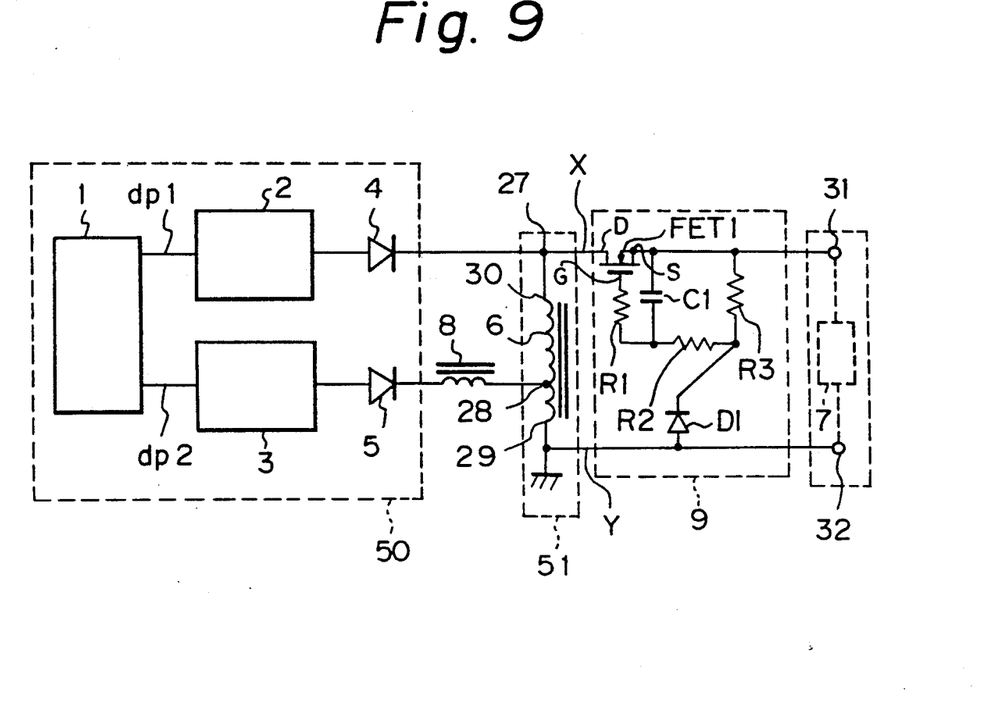
FIG. 9 is a diagram of a circuit of a fourth embodiment of the present invention.

The fourth embodiment of the present invention provides a device having a circuit eliminating such a direct current component.

This will be explained with reference to FIG. 9.

As shown in FIG. 9, almost all the components are the same as used in FIG. 1 except for a circuit 9 for eliminating a direct current component provided between the coil means 51 and the electrode means 52.

The circuit 9 includes at least an FET transistor FET 1, a capacitor C1, and a diode D1.

A drain D of the FET 1 is connected to an input x of the circuit 9, and a source S thereof connected to one end of the capacitor C1, while a gate of the FET 1 is connected to the other end of the capacitor C1 through a resistor R1.

On the other hand, an anode of the diode D1 is connected to another input y of the circuit 9, and a cathode thereof connected to one end of the capacitor C1 through a resistor R3 and to another end of the capacitor C1 through a resistor R2.

As shown in FIG. 9, the output of the cathode of the diode 4 is connected to the input x of the circuit 9, i.e., connected to the drain of the FET 1, while the input y is connected to one end of a coil 6 and thereby grounded.

According to this circuit 9, when a low frequency driving pulse dp1 is generated from the signal control means 1, it is amplified by the current amplifying circuit 2 and applied to the coil means 51, for example, a coil 6, through the diode 4 as an exciting current.

At this time, the transistor FET 1 is OFF, so the current flowing to the load 7 is interrupted since the voltages between the anode and cathode of the diode D1 and between the gate and source of the transistor FET 1 are kept at the same potential.

When application of the exciting current to the coil 6, is interrupted, a counter electromotive voltage is generated in the output voltage as shown in FIG. 10(b), whereby a forward voltage is applied to the diode D1 to turn the transistor FET 1 ON and the capacitor C1 is charged.

The electric charge in the capacitor C1 turns the transistor FET 1 ON during a time defined by a time constant based upon the capacitor C1 and the resistors R2 and R3 after the diode D1 is turned OFF.

Therefore, the direct current component (e), i.e., a forward voltage, can be eliminated from the output voltage obtained across the coil 6 applied to the load 7 between the electrodes 31 and 32.

In this embodiment, an FET transistor is used in the circuit 9, but a bipolar transistor can also be used.

A fifth embodiment will be explained with reference to FIG. 11.

Figure 11:
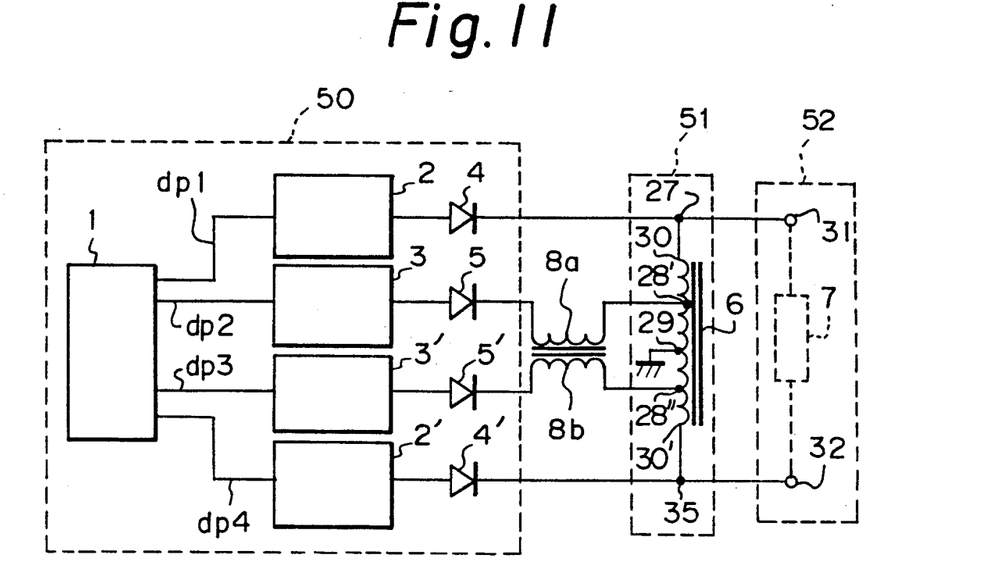
FIGS. 11 and 12 are diagrams of circuits of fifth and sixth embodiments of the present invention, respectively.

As shown in FIG. 11, the bio-stimulating device of the fifth embodiment includes mainly two of the circuit constructions explained above.

Note that in FIG. 11, pulse signals dp1 and dp4 output from a signal control means 1 are driving pulses having a low frequency, while pulse signals dp2 and dp3 are driving pulses having a rectangular waveform and a high frequency.

The driving pulse signals dp1 to dp4 are connected to inputs of current amplifying circuits 2, 3, 3', and 2', respectively.

The outputs thereof are connected to anodes of diodes 4, 5, 5', and 4'.

A cathode of the diode 4 is connected to one end 27 of a coil 6 of a coil means 51 and an electrode 31, while a cathode of the diode 5 is connected to one end of a coil 8a.

The other end is connected to a tapped portion 28' of the coil 6.

A cathode of the diode 4' is connected to one end 35 of a coil 6 of a coil means 51 and an electrode 32, while a cathode of the diode 5' is connected to one end of a coil 8b.

The other end thereof is connected to a tapped portion 28'' of the coil 6.

As apparent from FIG. 11, a center tapped portion 29 is connected to ground.

Namely, in this embodiment, two tapped portions 28' and 28'' are provided between the center tapped portion 29 and the ends 27 and 35 of the coil 6.

The two circuit constructions of the bio-stimulating device are combined to make one unit and drive one coil 6.

Figure 12:
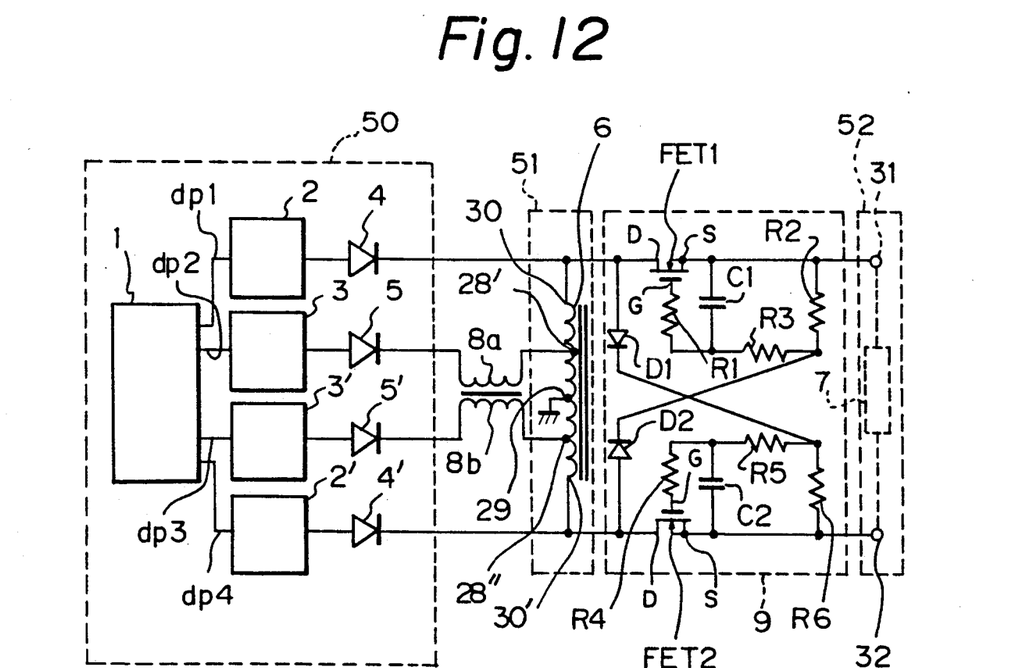

A sixth embodiment of the present invention is shown in FIG. 12.

The bio-stimulating device of the sixth embodiment mainly includes the same circuit construction as explained in the fifth embodiment, except having a circuit 9 for eliminating a direct current component provided between the coil means 51 and the electrode means 52.

Note that, in FIG. 12, an output 27 of the coil means 51 is connected to an anode of a diode D1 and a drain D of a transistor FET 1, while another output 35 of the coil means 51 is connected to an anode of a diode D2 and a drain D of a transistor FET 2.

A gate of the FET 1 is connected to one end of a resistor R1.

The other end of the resistor R1 is connected to one end of a capacitor C1 and one end of a resistor R3.

The other end of the resistor R3 is connected to an end of the resistor R2 and a cathode of a diode D2.

The other end of the resistor R2 is connected to a source S of the FET 1, the other end of the capacitor C1, and an electrode 31.

On the other hand, a gate of the FET 2 is connected to one end of a resistor R4.

The other end of the resistor R4 is connected to one end of a capacitor C2 and one end of a resistor R5.

The other end of the resistor R5 is connected to the other end of the resistor R6 and a cathode of a diode D1.

The other end of the resistor R6 is connected to a source S of the FET 2, the other end of the capacitor C2, and an electrode 32.

The direct current component eliminating circuit 9 can eliminate the direct current component from the output voltage generated across the electrodes to eliminate the uncomfortable feeling caused by that component in the same way as the fourth embodiment.

Note that in the sixth embodiment, both the exciting currents generated by of the driving pulse signals dp1 and dp4 and flown in the coil 6, are prevented form flowing to the electrode means 52 by turning the FET 1 and FET 2 OFF when the driving signals are input to this circuit.

In this embodiment, either the low frequency driving pulse or the high frequency driving pulse is used for the therapy by utilizing a suitable switching means provided in the signal control means 50, preferably associated with the digital signal control circuit 1 including a microcomputer or the like.

For example, when a user wishes to use a low frequency pulse, one of the driving pulses dp1 and dp4 is selected by the switching means.

The frequency of the pulses is changeable and the desired frequency can be easily set by a suitable means provided in the signal control means.

Further, the frequency of the two driving pulses may be set at the same level or at different levels.

In this case, when the driving pulse dp1 is used, the polarity of the signal voltage output from the electrodes means 52 is opposite to that of the voltage when the driving pulse dp4 is used, since the direction of current flow through the coil 6 is reversed.

The driving pulse dp1 or dp4 is therefore selected depending upon which polarity of the output voltage the use prefers.

The two driving pulses dp1 and dp4 may also be used simultaneously.

In such a case, the driving pulses dp1 and dp4 are preferably given a phase difference of 180 degrees when the pulses have the same frequency.

On the other hand, when the high frequency driving pulse is intended to be used the driving pulses dp2 and dp3 are simultaneously selected and used.

Namely in this case, the frequency of the pulses dp2 and dp3 are made slightly different to generate low frequency interference pulse wave between the electrodes 31 and 32.

For example, when the driving pulse dp2 has a frequency of 4000 Hz, the other driving pulse dp3 may have a frequency of 4032 Hz to generate a low frequency interference wave having a low frequency of 32 Hz.

Figure 13A:
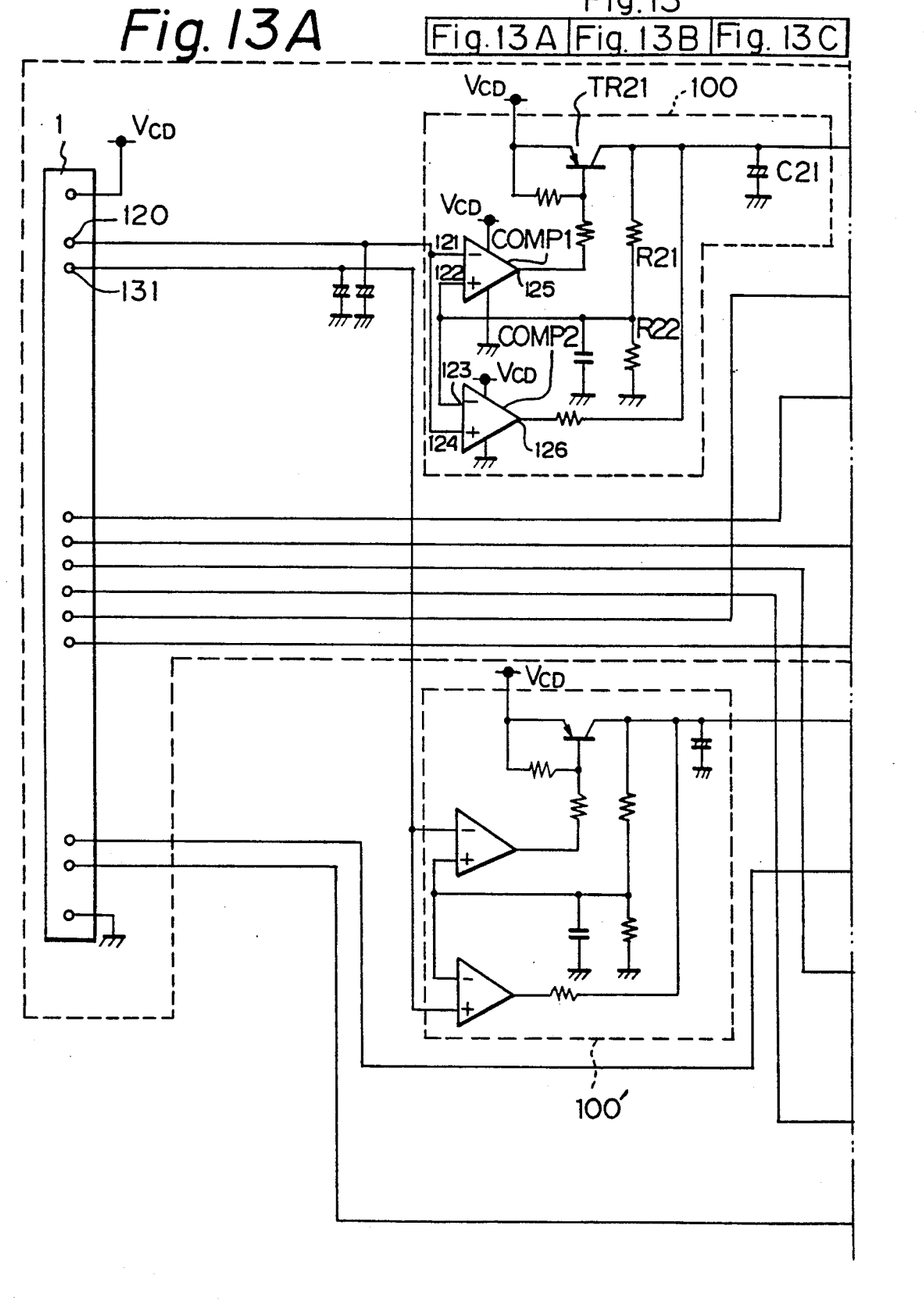
FIGS. 13(a) through 13(c) is a diagram of a seventh embodiment of the present invention.
Figure 13B:
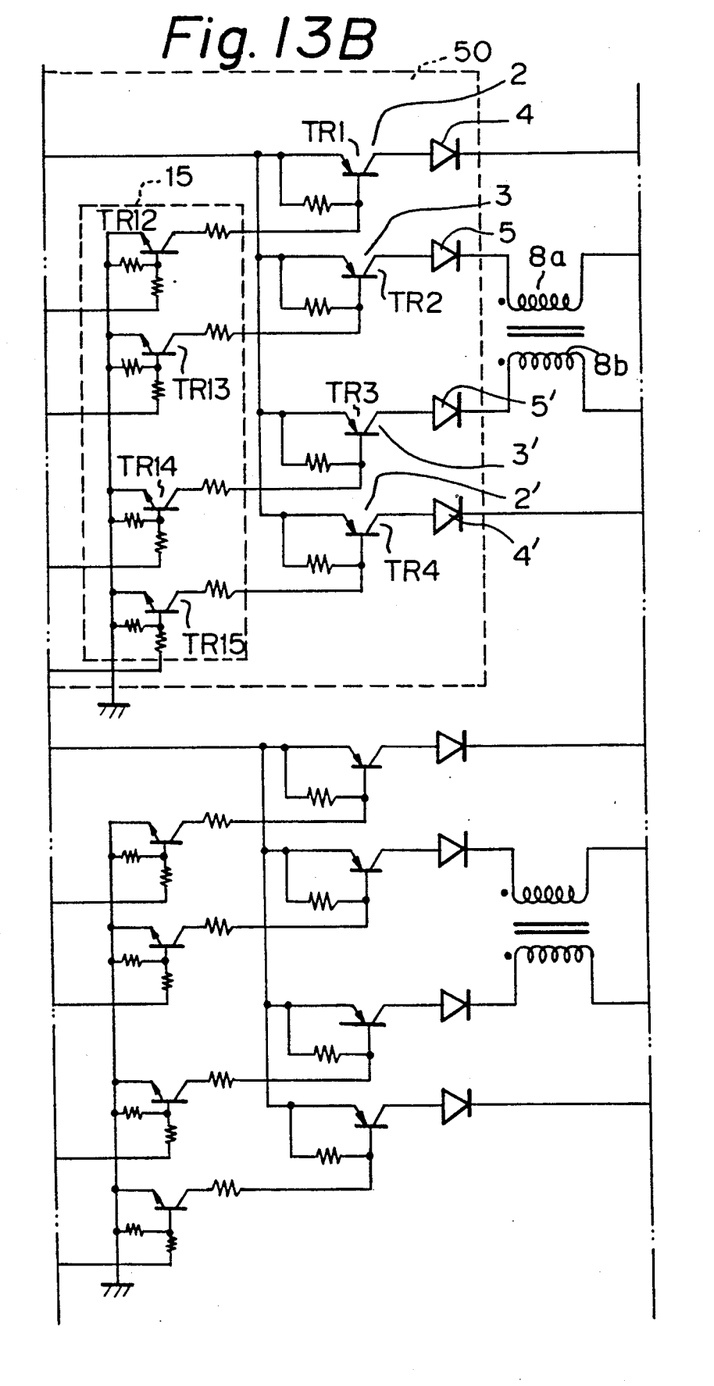
Figure 13C:
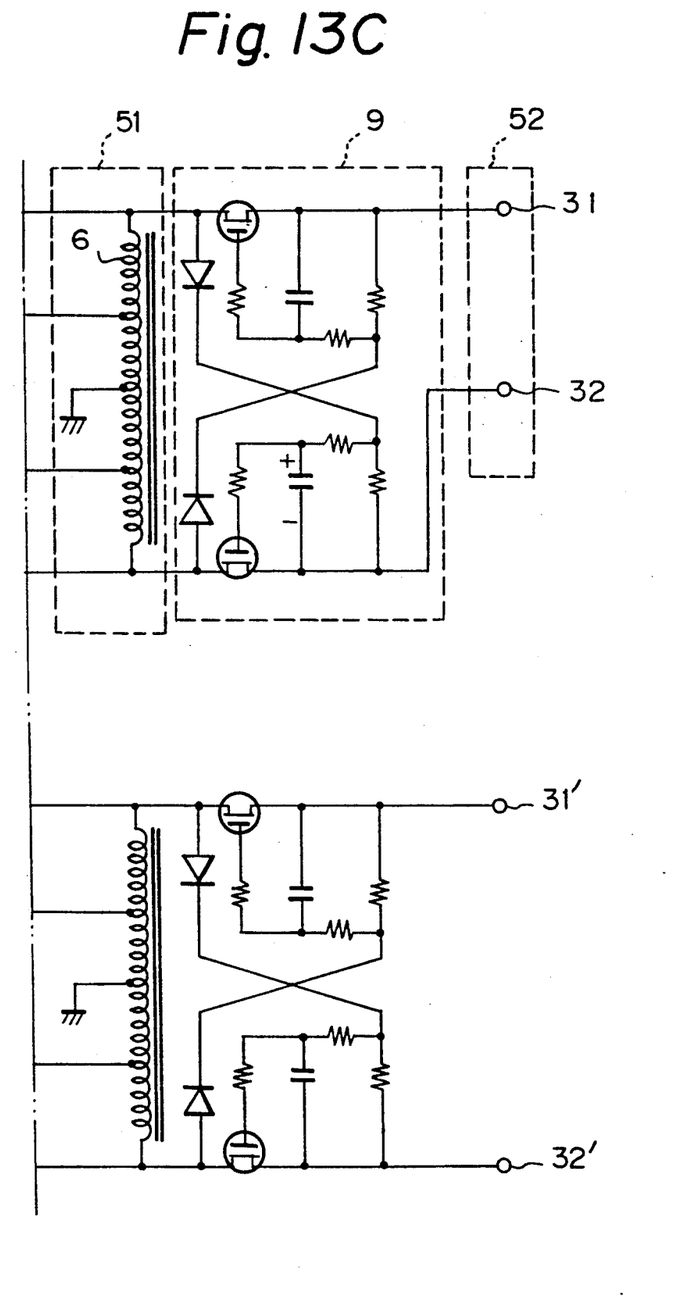

A seventh embodiment of the present invention will be explained with reference to FIG. 13.

In this embodiment, the bio-stimulating device has two independent devices each the same as shown in FIG. 12.

This type of device is suited for use for therapy utilizing high frequency pulse signals such as dp2 and dp3.

As explained above, when both the high frequency pulse signals dp2 and dp3 are used, a low frequency wave is generated across the electrodes 31 and 32 therefore, the same situation occurs in the other device, i.e., another low frequency wave is generated across the electrodes 31' and 32'.

In this case, the low frequency waves may have the same or different frequencies.

When the two pairs of the electrodes 31 and 32 and 31' and 32' are placed on the human body, for example, so that the current path across one pair of electrodes intersects the current path across the opposite pair, a further interference low frequency wave can be generated among the electrodes to stimulate the body.

In the seventh embodiment, the amplifying circuits 2, 3, 3', and 2' include PNP transistors TR1, TR2, TR3, and TR4 respectively.

An emitter of each transistor is connected to a source voltage $V_{CD}$ through a voltage adjusting circuit 100, explained later.

The bases thereof are connected to collectors of switching transistors TR12, TR13, TR14, and TR15 respectively.

The switching transistors are turned on and off with low and high frequency driving pulses respectively, utilizing a suitable switching circuit provided in a microcomputer or the like in the data signal control means 1.

In these embodiments, a single coil 6 is used as the a coil means, but two electromagnetically coupled coils may also be used.

Further, when a low frequency pulse wave is used, the frequency of the stimulating wave output from the electrodes 31 and 32 may be set, for example, at 250 Hz, 32 Hz or 16 to 1 Hz and the voltage thereof may be set, for example, at 1 to 130 V.

On the other hand, when a high frequency pulse wave is used, the frequency of the stimulating wave at a first output, i.e., the electrode 31, for example, may be set at 4000 Hz, while the frequency of the stimulating wave at a second output, i.e., the electrode 32, for example, may be set at any one of 4000 Hz, 4002 Hz, 4004 Hz and 4032 Hz, so an interference wave having a low frequency of 1, 2, 4, and 32 Hz can be generated, respectively.

In each case, the amplitude of any output wave may be at most 60 V.

Further, a phase difference may be introduced between two high frequency pulse waves to generate such an interference wave instead of using the frequency difference, but a greater effect in generating such an interference wave is obtained utilizing the frequency difference.

In the present invention, a voltage adjusting circuit may be used for controlling the source voltage.

An explanation will be given of the voltage adjusting circuit hereunder.

The voltage adjusting circuit can adjust the source voltage supplied to the amplifying circuit, at a constant desired level.

The basic idea of the source voltage adjusting circuit is explained with reference to FIG. 14.

In the Fig., a data control circuit 101, for example, a microcomputer, is connected to a digital/analog converter 102.

The output analog signal is input to a voltage comparator circuit 103.

The output of the comparator 103 is connected to a source voltage supplying circuit 104.

The output of the source voltage supplying circuit 104 is applied to another input of the voltage comparator circuit 103.

Therefore, the output of the source voltage supplying circuit 104 can be controlled, and an adjusted source voltage for the bio-stimulating signal is output to the amplifying circuit 105, which corresponds to the amplifying circuits 2, 3, 3', and 2' shown in FIGS. 11 or 12.

Note that, in this voltage adjusting circuit, a digital pulse signal indicating information enabling the final output source voltage to be set at an intended level is first generated in the microcomputer or the like.

Toward this end, the frequency or duty ratio thereof can be changed.

Then, the digital signal is converted into an analog signal by the digital/analog converter 102, and the analog signal is used to control the output source voltage.

Figure 14:
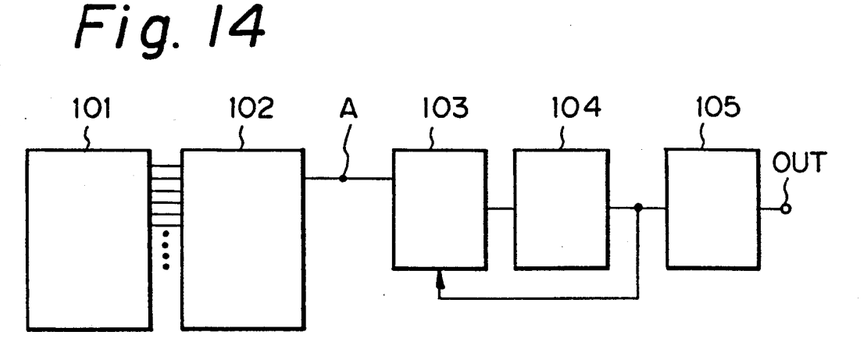
FIGS. 14, 15, and 16 show specific embodiments of a voltage adjusting means used in FIG. 13.
Figure 15:
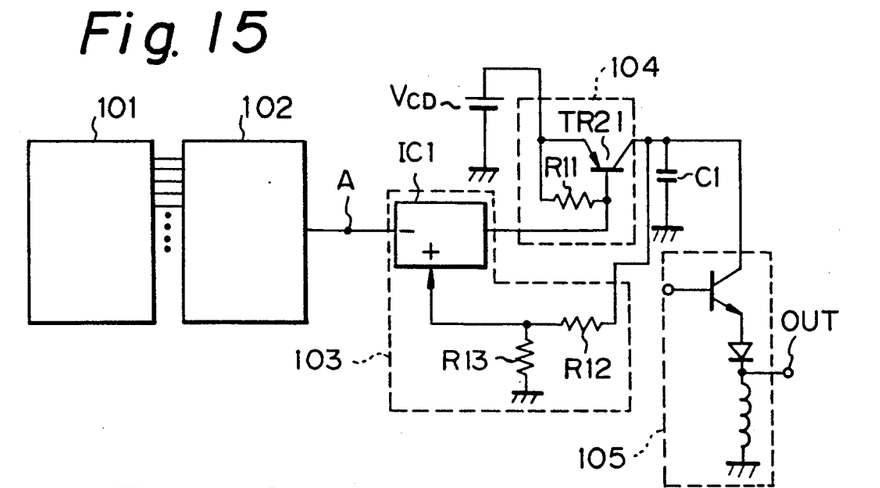

FIG. 15 shows a more specific circuit construction of the circuit shown in FIG. 14.

An output A from the digital/analog converter 102 is connected to a minus terminal (−) of a comparator IC1 in the comparator circuit 103, while a plus terminal (+) thereof is connected to one end of a resistor R12 and R13.

An emitter of a transistor TR21 and one end of a resistor R11 are connected to a plus terminal of a source voltage $V_{CD}$, while a collector of the transistor TR21 is connected to another end of the resistor R12 and one end of a capacitor C11 and further connected to an output means 105.

Another end of the capacitor C11 and the resistor R13 as well as a minus terminal (−) of the source voltage are connected to ground.

When an analog data is input to the minus terminal (−) of the comparator IC1 and a collector voltage of the transistor TR21 is input to the plus terminal (+) thereof divided by the resistor R12 and R13, the output of the collector is controlled so that a voltage value obtained by dividing the collector voltage of the transistor TR21 with the resistor R12 and R13 is always equal to a voltage value applied to the minus terminal (−) of the comparator IC1, since the output of the comparator IC1 is connected to the base of the transistor TR11.

Another example of this embodiment will be explained with reference to FIG. 16 hereunder.

Figure 16:
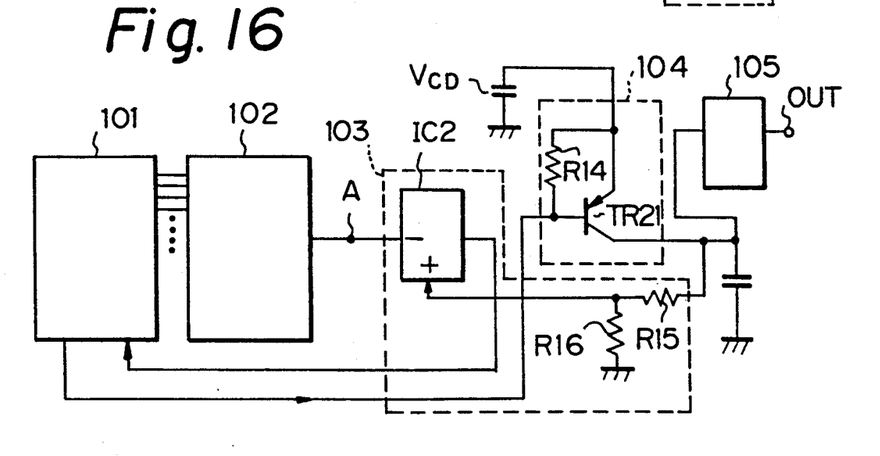

In FIG. 16, data A output from the microcomputer 101 or the like is applied to an input of the digital/analog converter 102.

The output of the digital/analog converter 102 is connected to a minus terminal (−) of a comparator IC2 of the comparing circuit 103 while a plus terminal (+) thereof is connected to one end of a resistor R15 and R16.

An output of the comparator IC2 is connected to an input of the microcomputer 101, while another output of the microcomputer 101 is connected to one end of a resistor R14 and a base of a transistor TR 21.

On the other hand, an emitter of the transistor TR 21 and another end of the resistor R14 are connected to a plus terminal (+) of a source voltage while a collector of the transistor TR 21 is connected to another end of the resistor R15 and one end of a capacitor C12 as well as an input of the amplifying circuit 105.

Another end of the capacitor C12 and the resistor R16 as well as a minus terminal (−) of the source voltage are connected to ground.

The analog signal A output from the digital/analog converter 102 is input to the minus terminal (−) of the comparator IC2, while a voltage obtained by dividing the collector voltage with the resistors R15 and R16 is input to the plus terminal (+) thereof.

On the other hand, an output of the comparator IC2 is input to the microcomputer 101.

The output thereof controls the output voltage of the collector of the transistor TR 21 so that a voltage value obtained by dividing the collector voltage of the transistor TR21 with the resistor R15 and R16 is always equal to a voltage value applied to the minus terminal (−) of the comparator IC2.

According to the present invention, the output voltage from the source voltage adjusting circuit 100 can be controlled by the analog signal generated from the digital signal control means 1 between 0 V and at most $V_{CD}$, for example, 5 V or the like.

A more specific circuit construction of the present invention especially with respect to the voltage adjusting circuit will be explained with reference to FIG. 13 hereunder.

Voltage adjusting circuits 100 and 100' are provided between a microcomputer 1 and amplifying circuits 2, 3, 3', and 2'.

The voltage adjusting circuits are connected to a voltage source $V_{CD}$.

In the microcomputer 1, a digital/analog converter is provided.

The output thereof is connected to the input of the voltage adjusting circuits.

Looking at just the circuit 100, two comparators COMP1 and COMP2 are provided.

An analog signal A output from the output 120 of the digital/analog converter provided in the microcomputer 1 is input to an inverting terminal 121 of the comparator COMP1 and to a non-inverting terminal 124 of the comparator COMP2.

An output 125 of the comparator COMP1 is connected to a base of a transistor TR21, an emitter of which is connected to a voltage source $V_{CD}$ and a collector of which is connected to one end of a capacitor C21 and inputs of the amplifying circuits 2, 3, 3', and 2'.

On the other hand, an output 126 of the comparator COMP2 is connected to the collector of the transistor TR21 and one end of a capacitor C21.

The output voltage of the transistor TR21 is divided by resistors R21 and R22.

The resultant voltage is input to non-inverting terminal 122 of the comparator COMP1 and to an inverting terminal 123 of the comparator COMP2 simultaneously.

According to this embodiment, when an analog signal input to the voltage adjusting circuit is varied increasingly or decreasingly, the output voltage of the transistor TR21, which is defined by the capacitor C21, is controlled by both comparators COMP1 and COMP2 in such a way that the voltage of the analog signal input to one of the terminal thereof always become equal to the voltage obtained by dividing the collector voltage of the transistor TR21 with the resistors R21 and R22.

The same explanations applies to the other voltage adjusting circuit 100'.

Figure 17A:
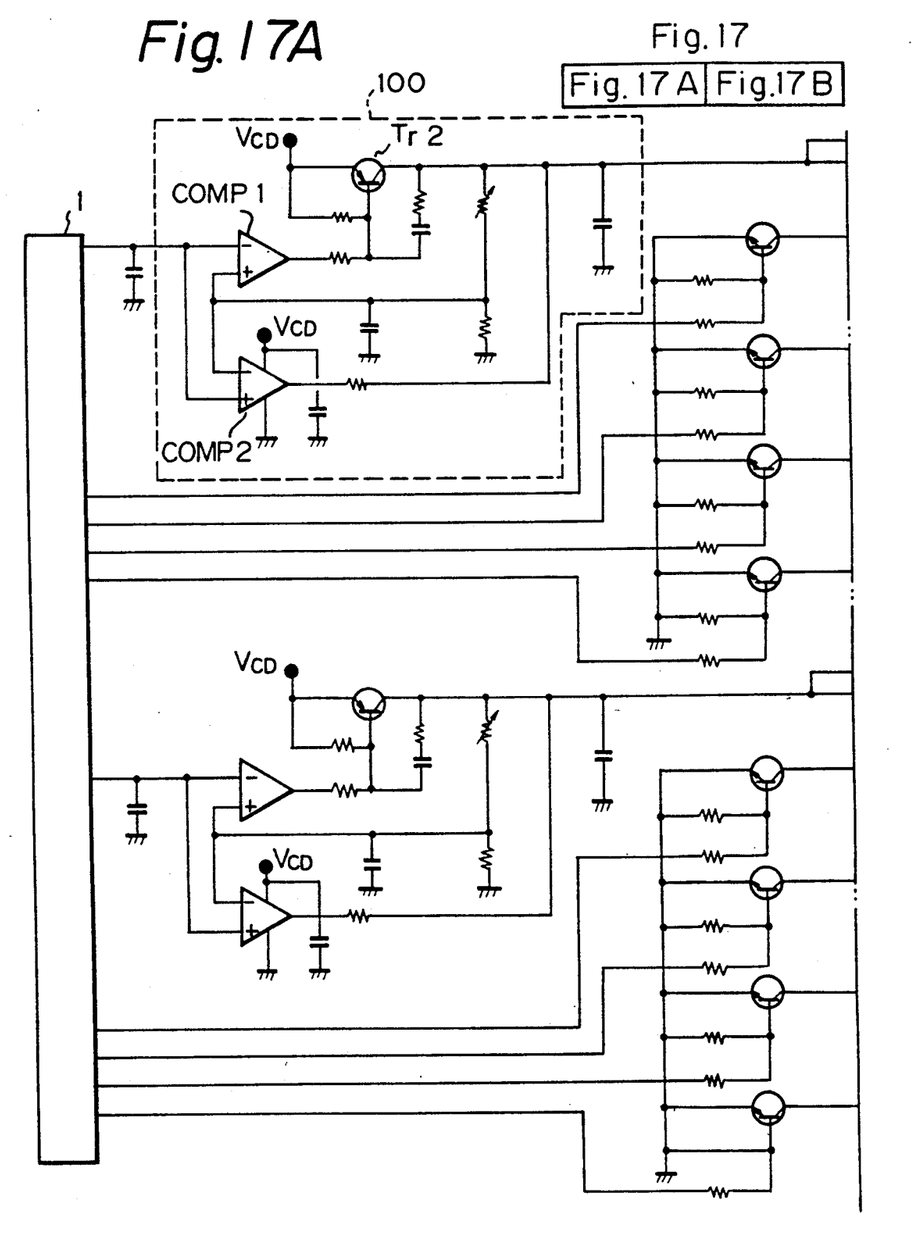
FIGS. 17(a) and 17(b) is a diagram of an eighth embodiment of the present invention.
Figure 17B:
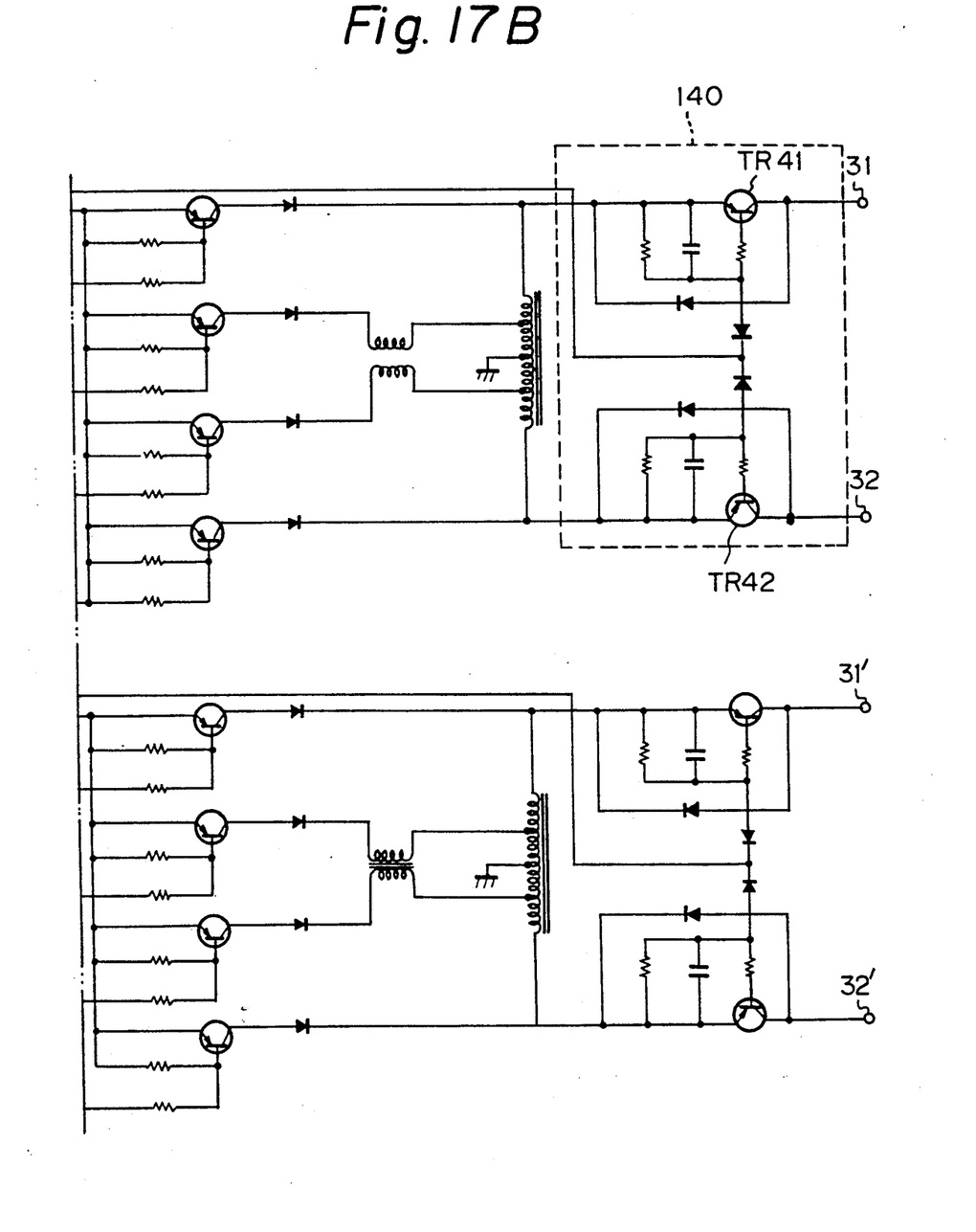

The last embodiment of the present invention will be explained with reference to FIG. 17 hereunder.

The direct current component eliminating circuit 140 includes two bipolar transistors TR41 and TR42, the bases thereof being mutually connected through diodes D24 and D25.

Between the diodes, is connected the output of the source voltage adjusting circuit.

On the other hand, an anode of a diode D20 is connected to a collector of the transistor TR41, a cathode thereof is connected to an emitter of the transistor TR41, an anode of a diode D21 is connected to a collector of the transistor TR42, and a cathode thereof is connected to an emitter of the transistor TR42.

The rest of the circuit construction is the same as explained in FIGS. 9 and 12.

According to the present invention amplified pulses suitable for use in the therapy can be obtained reasonably with considerable energy savings and reduced size of the device by utilizing the coil means for multiple purposes.

We claim:

1. A bio-stimulating device which comprises a signal control means for outputting at least a high frequency digital signal and a low frequency digital signal, a coil means for changing the voltage of the digital signals input thereto from said control means and having a first voltage changing function for the high frequency digital signals and a second voltage changing function for the low frequency digital signals, and an electrode means connected to the coil means to be attached to a body for applying stimulating pulsed voltage thereto.

2. The bio-stimulating device of claim 1, wherein said signal control means comprises a means for controlling at least a frequency and a duty ratio of said high and low frequency digital signals and amplifiers for amplifying the high and low frequency digital signals output therefrom.

3. The bio-stimulating device of claim 1, wherein said signal control means comprises a microcomputer.

4. The bio-stimulating device of claim 1, wherein said coil means comprises at least one coil formed to have a primary coil portion and a secondary coil portion, said first voltage changing function of said coil means being effected by inputting said high frequency digital signals into the primary coil portion, said primary coil portion having a smaller winding number than that of said secondary coil portion, to amplify the voltage of said high frequency digital signals output from the ends of said secondary coil portion in accordance with the winding ratio of the coil portions, while said second voltage changing function is effected by inputting said low frequency digital signals at one end of said secondary coil portion to amplify the voltage of said low frequency digital signals by a counter electromotive force caused by stopping the supply of the electric current to said at least one coil intermittently.

5. The bio-stimulating device of claim 4, wherein said two different voltage changing functions are carried out in one coil.

6. The bio-stimulating device of claim 5, wherein said coil has a tap portion to which said high frequency digital signals are input.

7. The bio-stimulating device of claim 4, wherein said two different voltage changing functions are carried out by two coils electromagnetically coupled to each other.

8. The bio-stimulating device of claim 4, wherein said signal control means is provided with at least two output terminals, one for said high frequency digital signals and the other for said low frequency digital signals and including means for eliminating a peak current caused by a high frequency component of said signals output from said coil means located between the output terminal of said signal control means for said high frequency digital signals and its input to said coil means.

9. The bio-stimulating device of claim 4, including a means for eliminating a peak current caused by a high frequency component of said signals output from said coil means located between the coil means and said electrode means.

10. The bio-stimulating device of claim 4, including a means for eliminating a direct current component from signals output from said coil means when said low frequency digital signals are used located between said coil means and said electrode means.

11. The bio-stimulating device of claim 1, wherein said signal control means is provided with at last two output terminals, one for said high frequency digital signals and the other for said low frequency digital signals, and a switching means for selecting said high frequency digital signals and said low frequency digital signals.

12. The bio-stimulating device of claim 11, wherein said signal control means is further provided with a voltage adjusting means for adjusting to a desired level the voltage to be supplied to said coil means.

13. The bio-stimulating device of claim 12, wherein said switching means and said voltage adjusting means are controlled by a microcomputer provided in said signal control means.

14. The bio-stimulating device of claim 13, wherein said voltage adjusting means is controlled by an analog signal converted from digital signals output from said microcomputer by a digital/analog converter provided in said signal control means.

15. The bio-stimulating device of claim 11, wherein at least four output terminals are provided, two of them being used for said high frequency digital signals and two for said low frequency digital signals.

16. The bio-stimulating device of claim 15, wherein said coil means comprises one coil having at least three taps at predetermined intervals, a center tap being connected to the ground and the other two taps connected to the two terminals outputting said high frequency digital signals.

17. The bio-stimulating device of claim 16, wherein when said frequency digital signals are used, the two terminals for said signals are simultaneously switched ON.

18. The bio-stimulating device of claim 17, wherein the high frequency digital signals output from one of said two terminals are given a phase difference from the signals output from the other of said terminals to form a low frequency interference wave at said electrodes means.

19. The bio-stimulating device of claim 16, wherein when said low frequency digital signals are used, the two terminals for said signals are switched ON and wherein the digital signals output from one of the terminals are different in polarity from the signals output from the other of said terminals.

20. The bio-stimulating device of claim 1, including at least two of said signal control means, said coil means and said electrode means.

* * * * *